(12) United States Patent
LaBean et al.

(10) Patent No.: US 8,628,056 B2
(45) Date of Patent: Jan. 14, 2014

(54) DUAL SEALING SYSTEM FOR USE WITH A PROBE

(75) Inventors: Robert J. LaBean, Saginaw, MI (US); Gregory M. Olechowski, Bay City, MI (US); Jason D. Hatton, Essexville, MI (US); John Miller Hess, III, Midland, MI (US); Robert Huber, Jr., Frankenmuth, MI (US)

(73) Assignee: AptarGroup, Inc., Crystal Lake, IL (US)

( * ) Notice: Subject to any disclaimer, the term of this patent is extended or adjusted under 35 U.S.C. 154(b) by 1234 days.

(21) Appl. No.: 12/322,425

(22) Filed: Feb. 2, 2009

(65) Prior Publication Data

US 2010/0193516 A1 Aug. 5, 2010

(51) Int. Cl.
*A61M 5/178* (2006.01)

(52) U.S. Cl.
USPC .................................. 251/149.1; 604/167.04

(58) Field of Classification Search
USPC .............. 251/149–149.1; 604/167.01–167.04
See application file for complete search history.

(56) References Cited

U.S. PATENT DOCUMENTS

| | | | |
|---|---|---|---|
| 4,909,798 A | 3/1990 | Fleischhacker et al. | |
| 5,000,745 A * | 3/1991 | Guest et al. | 604/256 |
| 5,053,016 A | 10/1991 | Lander | |
| 5,062,648 A | 11/1991 | Gomringer | |
| 5,176,652 A * | 1/1993 | Littrell | 604/167.04 |
| 5,271,531 A | 12/1993 | Rohr et al. | |
| 5,312,362 A | 5/1994 | Pfolsgraf et al. | |
| 5,322,518 A * | 6/1994 | Schneider et al. | 604/247 |
| 5,409,464 A * | 4/1995 | Villalobos | 604/167.04 |
| 5,456,284 A | 10/1995 | Ryan et al. | |
| 5,458,640 A | 10/1995 | Gerrone | |
| 5,490,503 A | 2/1996 | Hollister | |
| 5,582,161 A | 12/1996 | Kee | |
| 5,603,702 A * | 2/1997 | Smith et al. | 251/149.1 |
| 5,709,664 A | 1/1998 | Vandenbroek et al. | |
| 5,727,770 A | 3/1998 | Dennis | |
| 5,752,938 A | 5/1998 | Flatland et al. | |

(Continued)

FOREIGN PATENT DOCUMENTS

EP   1 239 909 B1   8/2005

OTHER PUBLICATIONS

U.S. Appl. No. 12/070,799, filed Feb. 21, 2008, Gaus.
U.S. Appl. No. 12/268,814, filed Nov. 11, 2008, Gaus.

(Continued)

*Primary Examiner* — John Bastianelli
(74) *Attorney, Agent, or Firm* — Wood, Phillips, Katz, Clark & Mortimer (57) ABSTRACT

A dual sealing system (20) is provided for use with a probe (21) to allow access to an interior space (34) from an exterior environment (32). The system (20) includes a housing (22) defining a port (24) extending along a longitudinal axis (26) between an exterior end (28) of the housing and an interior end (30) of the housing to establish communication between an exterior environment (32) and an interior space (34); a first flexible, resilient penetratable member (40) extending across the port at a first location along the axis, the first penetratable member configured to create a seal around the probe with the probe inserted therethrough; and a second flexible, penetratable member (42) extending across the port at a second location along the axis spaced toward the interior end from the first location, the second penetratable member configured to create a seal after having been penetrated by the probe and the probe has been removed from the second penetratable member.

20 Claims, 9 Drawing Sheets

(56) References Cited

U.S. PATENT DOCUMENTS

| | | | |
|---|---|---|---|
| 5,895,377 A * | 4/1999 | Smith et al. ............... 604/256 |
| 5,927,566 A | 7/1999 | Mueller |
| 5,934,512 A | 8/1999 | Lampe et al. |
| 6,168,758 B1 | 1/2001 | Forsberg et al. |
| 6,227,200 B1 | 5/2001 | Crump et al. |
| 6,258,065 B1 | 7/2001 | Dennis et al. |
| 6,269,986 B1 | 8/2001 | Gross |
| 6,482,181 B1 | 11/2002 | Racenet et al. |
| 6,530,504 B2 * | 3/2003 | Socier ........................ 222/494 |
| 6,543,451 B1 | 4/2003 | Crump et al. |
| 6,616,016 B2 | 9/2003 | Hicks et al. |
| 6,629,530 B2 | 10/2003 | Cise |
| 6,860,869 B2 * | 3/2005 | Dennis ................... 604/167.03 |
| 7,152,603 B1 | 12/2006 | Crump et al. |
| 7,263,997 B2 | 9/2007 | Madsen et al. |
| 2002/0010436 A1 * | 1/2002 | Becker et al. ............... 604/256 |
| 2003/0195472 A1 | 10/2003 | Green et al. |
| 2007/0113855 A1 | 5/2007 | Carlsen |
| 2008/0237278 A1 | 10/2008 | Gaus et al. |

OTHER PUBLICATIONS

International Search Report and Written Opinion of international application PCT/US2010/00146.

\* cited by examiner

DUAL SEALING SYSTEM FOR USE WITH A PROBE

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

The present invention relates generally to sealing systems that allow a probe to selectively access an interior space from an exterior environment while maintaining a seal between the exterior environment and the interior space.

BACKGROUND OF THE INVENTION

Sealing systems that allow a probe to access an interior space or volume from an exterior environment are known and come in many forms. In this regard, some of such systems are designed to accommodate a probe that allows the passage of a fluent material to or from the interior space or volume, while other such systems are configured to allow access by a probe that has a sensor or other apparatus for providing information about the conditions within the interior space, such as, for example, the temperatures within the interior space, the pressures within the interior space, or the condition of visual indicators within the interior space. Yet other such systems are designed to accommodate probes that can either carry a sensor or allow the passage of a fluent material or both.

Some of the known systems utilize a flexible, resilient valve. One type of flexible, resilient, valve is a self-closing, slit-type valve mounted in a port of a fluent tube or container. Such valves have a slit or slits which define a normally closed orifice that opens to permit access therethrough in response to a probe, such as a fill/drain tool, inserted through the valve, or an increased pressure differential across the valve (e.g., resulting from an increased pressure within the container when the container is squeezed, or from a reduced external ambient pressure compared to the pressure within the container). Such valves are typically designed so that they automatically close to shut off flow therethrough upon removal of the probe or a reduction of the increased internal pressure within the container, or upon an increase of the external pressure. Designs of such valves and of sealing systems using such valves are illustrated in the U.S. Pat. Nos. 5,271,531, 5,927,566, and 5,934,512. Typically, the system includes a body or base that defines a seat for receiving the valve and includes a retaining ring or other structure for holding the valve on the seat in the base. See, for example, U.S. Pat. Nos. 6,269,986 and 6,616,016. Other such valve systems for use with a probe or fill/drain tool are shown in commonly owned U.S. patent application Ser. No. 12/070,799 titled VALVE MOUNTING ASSEMBLY WITH SLIT MISALIGNMENT PREVENTION FEATURE, filed Feb. 21, 2008 and naming David J. Gaus as inventor, and U.S. patent application Ser. No. 12/268,814 titled PORT CLOSURE SYSTEM WITH HYDRAULIC HAMMER RESISTANCE, filed Nov. 11, 2008 and naming David J. Gaus as inventor, the entire disclosures of which are incorporated herein by reference.

SUMMARY OF THE INVENTION

In accordance with one feature of the invention, a dual sealing system is provided for use with a probe to allow the probe to access an interior space from an exterior environment. The system includes a housing defining a port extending along a longitudinal axis between an exterior end of the housing and an interior end of the housing to establish communication between an exterior environment and an interior space; a first flexible, resilient penetratable member extending across the port at a first location along the axis, the first penetratable member configured to create a seal around the probe with the probe inserted therethrough; and a second flexible, penetratable member extending across the port at a second location along the axis spaced toward the interior end from the first location, the second penetratable member configured to create a seal after having been penetrated by the probe and the probe has been removed from the second penetratable member.

In one feature, at least one of the penetratable members includes at least one self-sealing slit through the penetratable member, and confronting, openable portions along the slit to define a normally closed orifice in an unconstrained condition wherein the openable portions can move toward the interior space to an open orifice configuration. As a further feature, the at least one self-sealing slit includes two self-sealing slits extending transverse to each other.

As one feature, the first penetratable member is configured to create a seal after having been penetrated by the probe and the probe has been removed from the second penetratable member, and the second penetratable member is configured to create a seal around the probe with the probe inserted therethrough.

According to one feature, the first and second penetratable members are identical in construction.

In one feature, the first and second penetratable members are separate components and the system further includes a spacer extending between the first and second penetratable members within the housing. As a further feature, the system further includes a retainer engaged with the housing to retain the penetratable members and the spacer within the housing.

According to one feature, the port and the penetratable members have circular cross sections transverse to the axis.

As one feature, each of the penetratable members has an interior side facing toward the interior space and defined by a convex surface.

In one feature, each of the penetratable members has an exterior side facing toward the exterior environment and defined by a concave surface. As a further feature, the concave surface is semispherical.

According to one feature, the system further includes first and second valves, each of the valves having a peripheral attachment portion mounted to the housing. The first valve further includes the first penetratable member in the form of a flexible, resilient head that extends from the peripheral attachment portion of the first valve, and the second valve further includes the second penetratable member in the form of a second flexible, resilient heat that extends from the peripheral attachment portion of the second valve.

In a further feature, each of the heads has at least one self-sealing slit through the head and confronting, openable portions along the slit to define an initially closed orifice wherein the valve head openable portions can move generally in a first direction toward the space to an open configuration, with each of the valves having an initial, manufactured configuration in which the valve orifice is closed. As yet a further feature, the at least one self-sealing slit of each head includes two self-sealing slits extending transverse to each other.

As a further feature, the housing further includes a seat around the port and the peripheral attachment portion of the second valve is engaged in the seat.

In yet a further feature, the system further includes a spacer sandwiched in the housing between the peripheral attachment portions of the first and second valves. As a further feature, the spacer further includes a seat and the peripheral attachment portion of the first valve is engaged in the seat. In a further feature, the system further includes a retainer ring in snap-fit engagement with the housing to clamp the peripheral attachment portions in their respective seats.

According to one feature, the first and second valves have identical constructions.

In one feature, each of the valves is initially separate from, but subsequently attachable to, the housing.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

DETAILED DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

As discussed in detail hereinafter, a dual sealing system of the present invention is particularly useful for medical applications that require the use of a probe in the form of a sensor or in the form of a fill/drain tool, such as, for example, are used in connection with a cannula and/or a medical port. In this regard, the dual valve system is particularly useful in such systems wherein the interior space is subject to a pressurization that is greater than the ambient pressure of the exterior environment. Additionally, the dual sealing system of the present invention can be used in a fluid handling system, including in an associated container or other dispensing structure so as to accommodate transfer of fluent substances including, but not limited to, water or other fluids suitable for consumption via a probe in the form of a fill/drain tool.

The dual sealing system of the present invention may be used with a variety of conventional or special fluent substance handling and/or holding systems, including cannulas, medical ports, flexible tubing, glass or plastic bottles, flexible tubular containment structures, containers, tanks, vessels, and other equipment or apparatus, the details of which, although not fully illustrated or described, would be apparent to those having skill in the art and an understanding of such systems. The particular fluent substance handling or holding system, per se, forms no part of, and therefore is not intended to limit, the broad aspects of the present invention. It will also be understood by those of ordinary skill that novel and non-obvious inventive aspects are embodied in the described exemplary dual sealing system alone.

Figure 4:
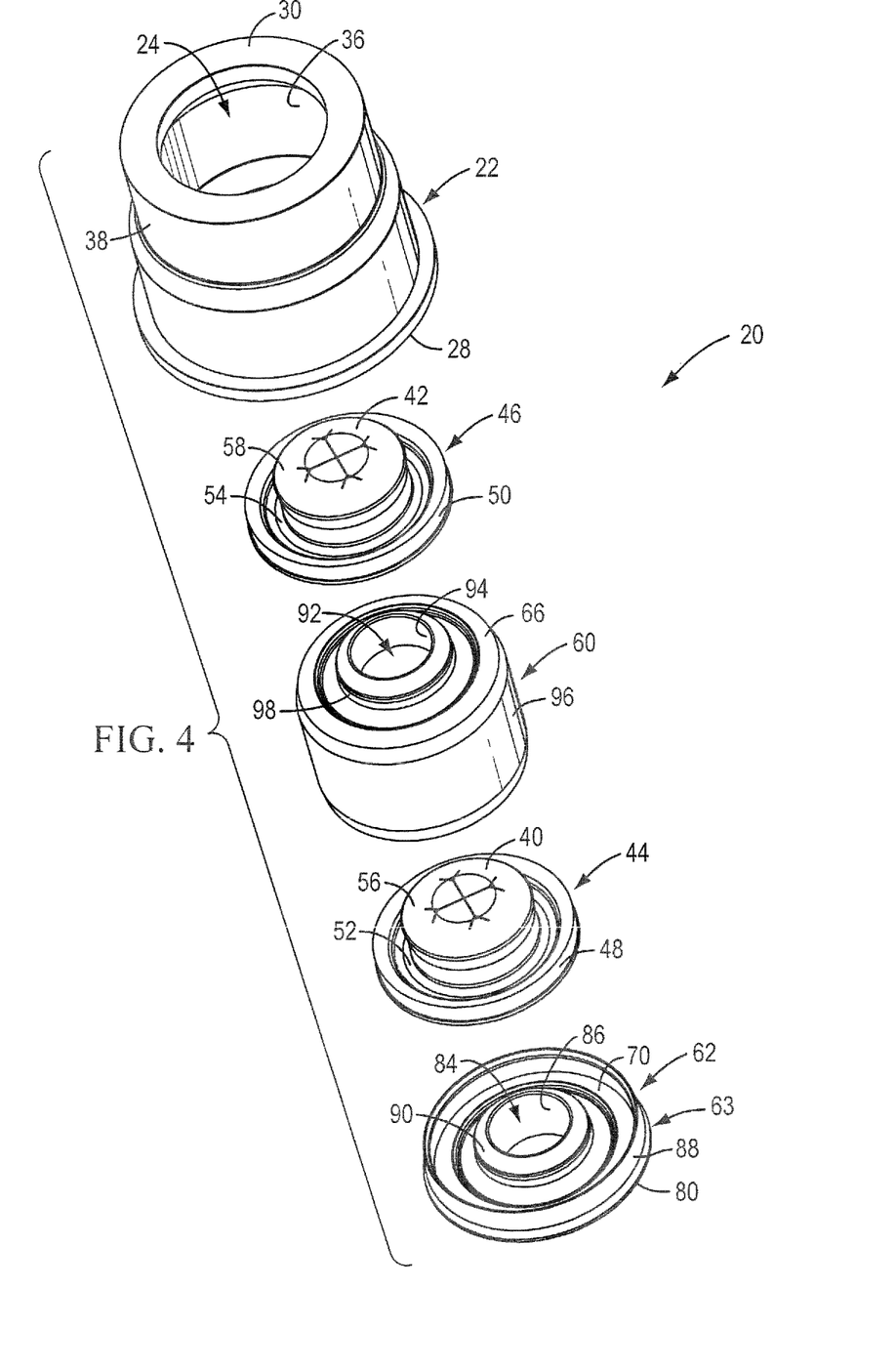
FIG. 4 is an exploded isometric view of the dual sealing system taken from the interior side.
Figure 5:
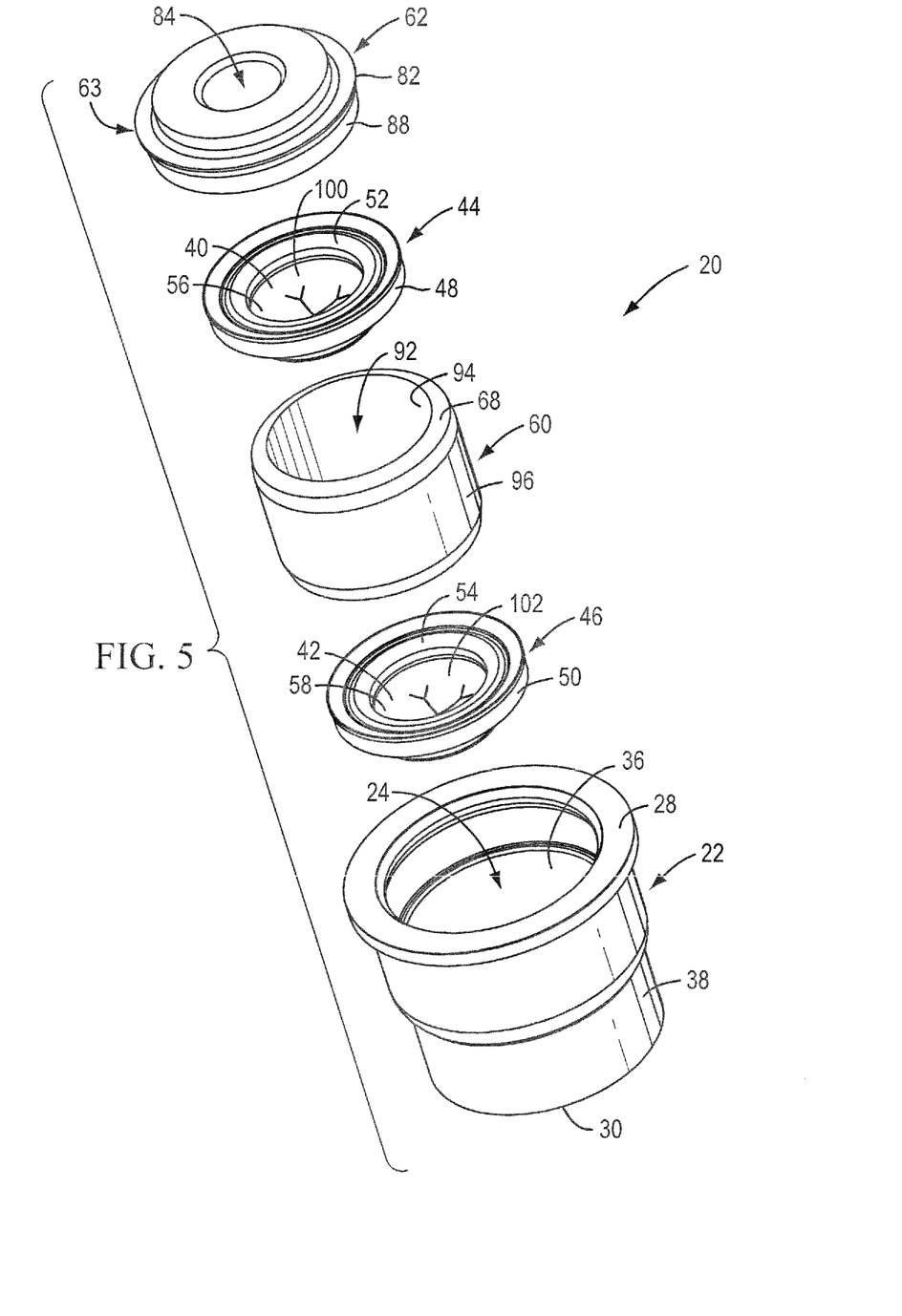
FIG. 5 is an exploded isometric view of the dual sealing system taken from the exterior side.
Figure 6:
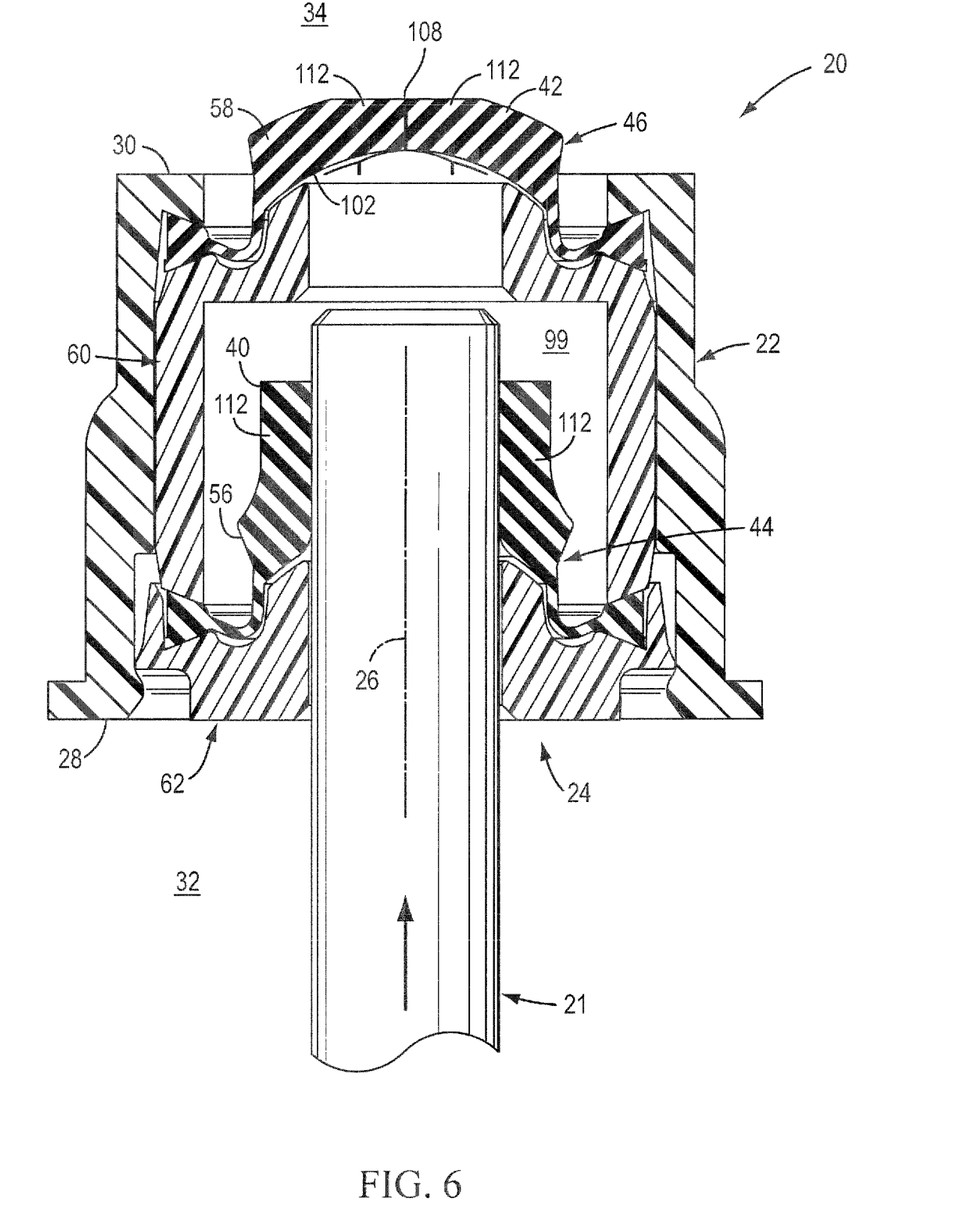
FIG. 6 is a view similar to FIG. 3, but showing a probe as it is being inserted part way into the dual sealing system.
Figure 7:
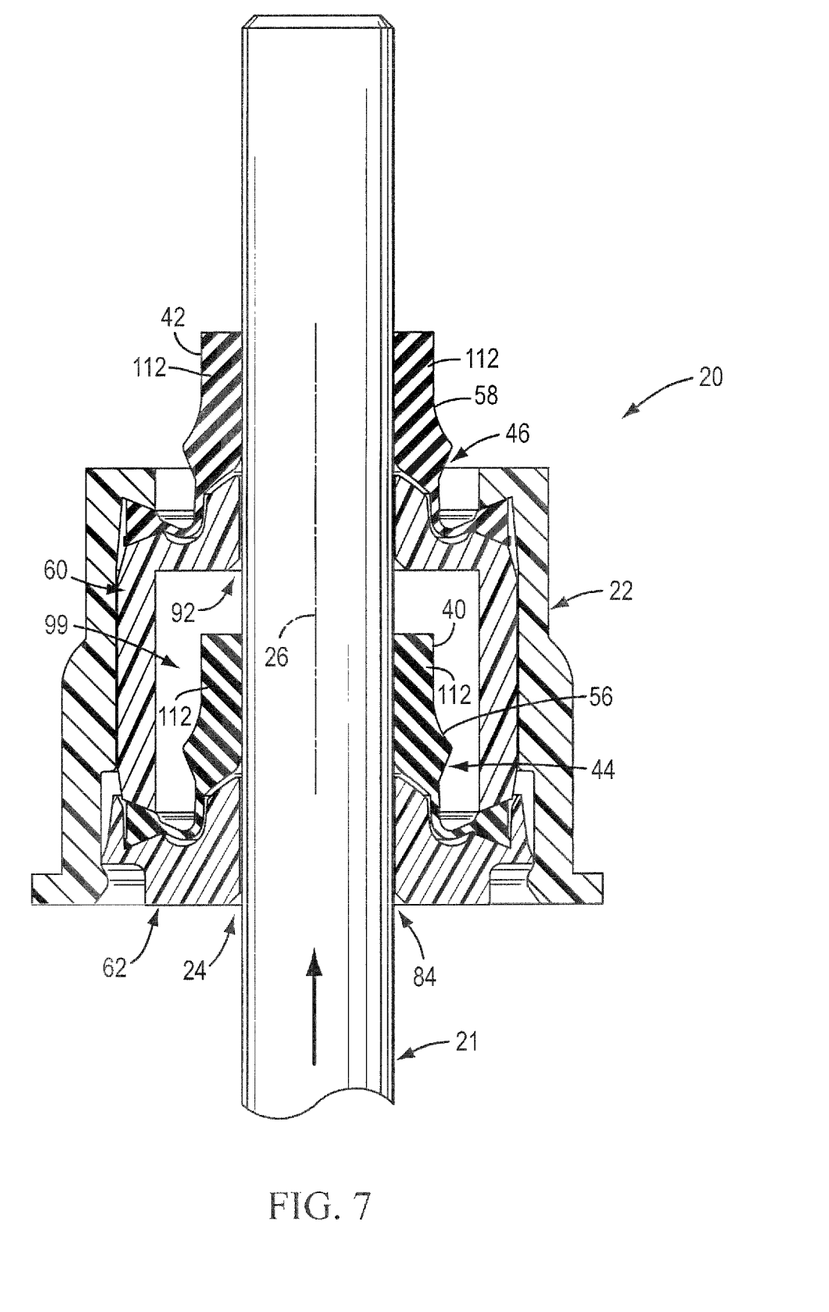
FIG. 7 is a view similar to FIG. 3, but showing the probe being completely inserted into the dual sealing system.
Figure 8:
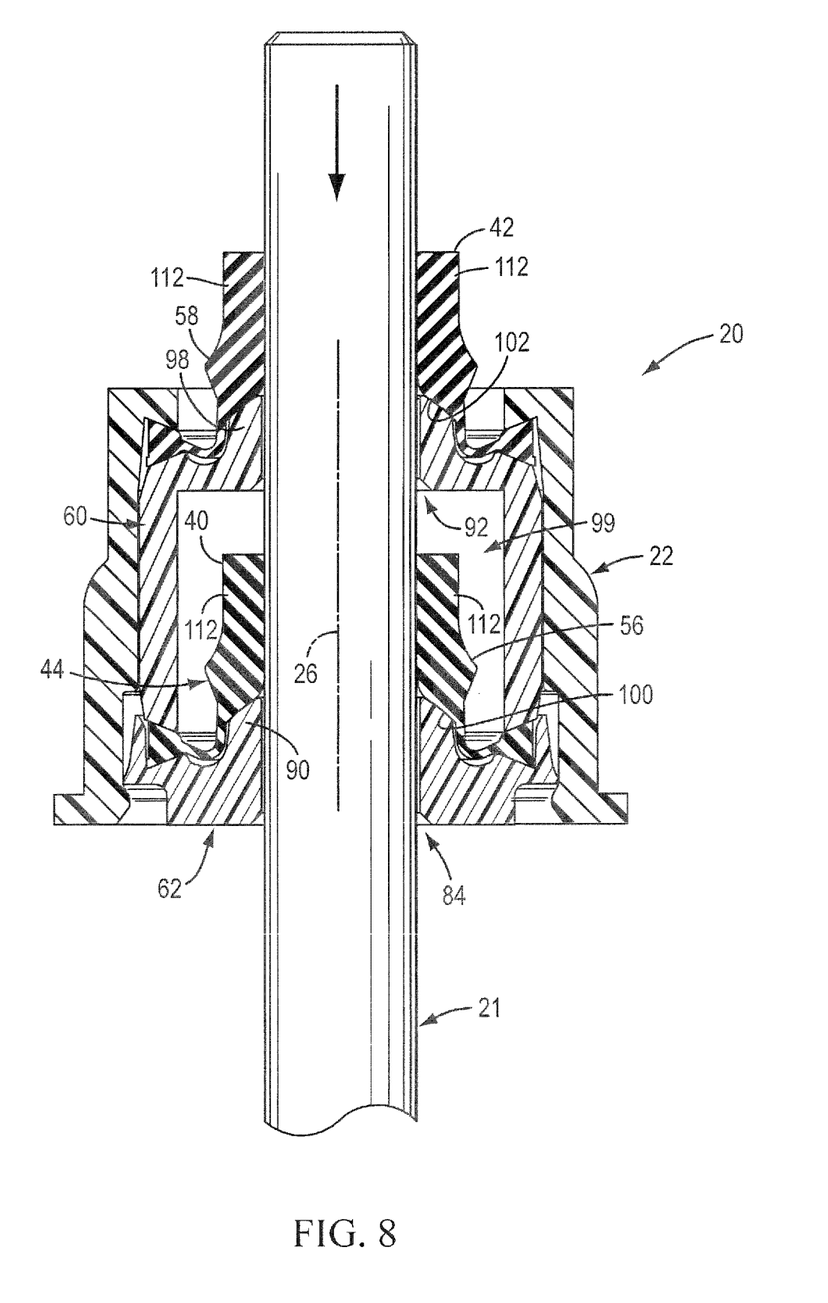
FIG. 8 is a view similar to FIG. 7, but showing the probe being extracted from the dual sealing system.

A presently preferred embodiment of the dual sealing system is illustrated in FIGS. 1-8 and is designated generally by the number 20. The system 20 is intended for use with a probe, generally designated by the number 21, which is illustrated in FIGS. 6-8 in a generic form. In this regard, it should be understood that there are many known types and constructions for the probe 21, including constructions wherein the probe 21 is a fill/drain tool, constructions where the probe 21 is a sensor or carries a sensor, and constructions wherein the probe 21 is a fill/drain tool that also carries or incorporates a sensor.

Figure 1:
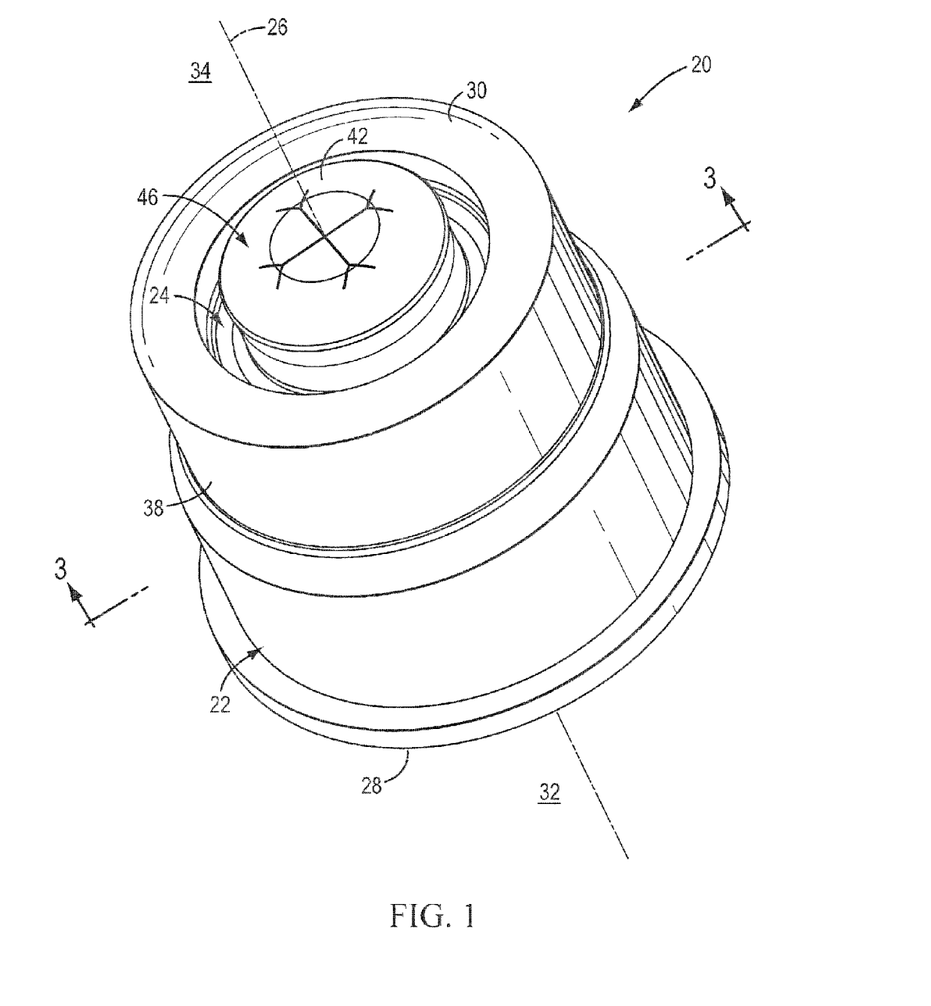
FIG. 1 is an isometric view taken from an interior side of a dual sealing system embodying the present invention.
Figure 2:
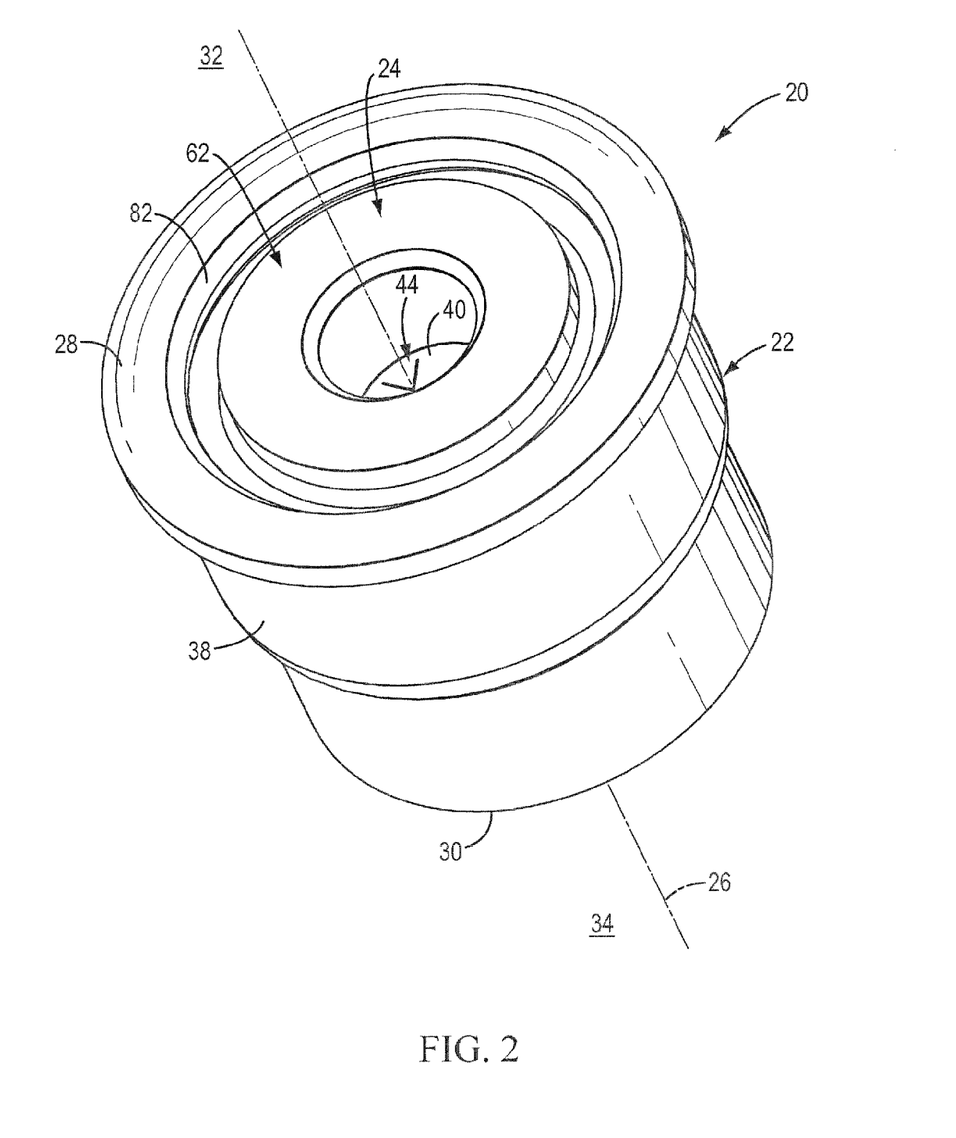
FIG. 2 is an isometric view from an exterior side of the dual valve sealing system of FIG. 1.
Figure 3:
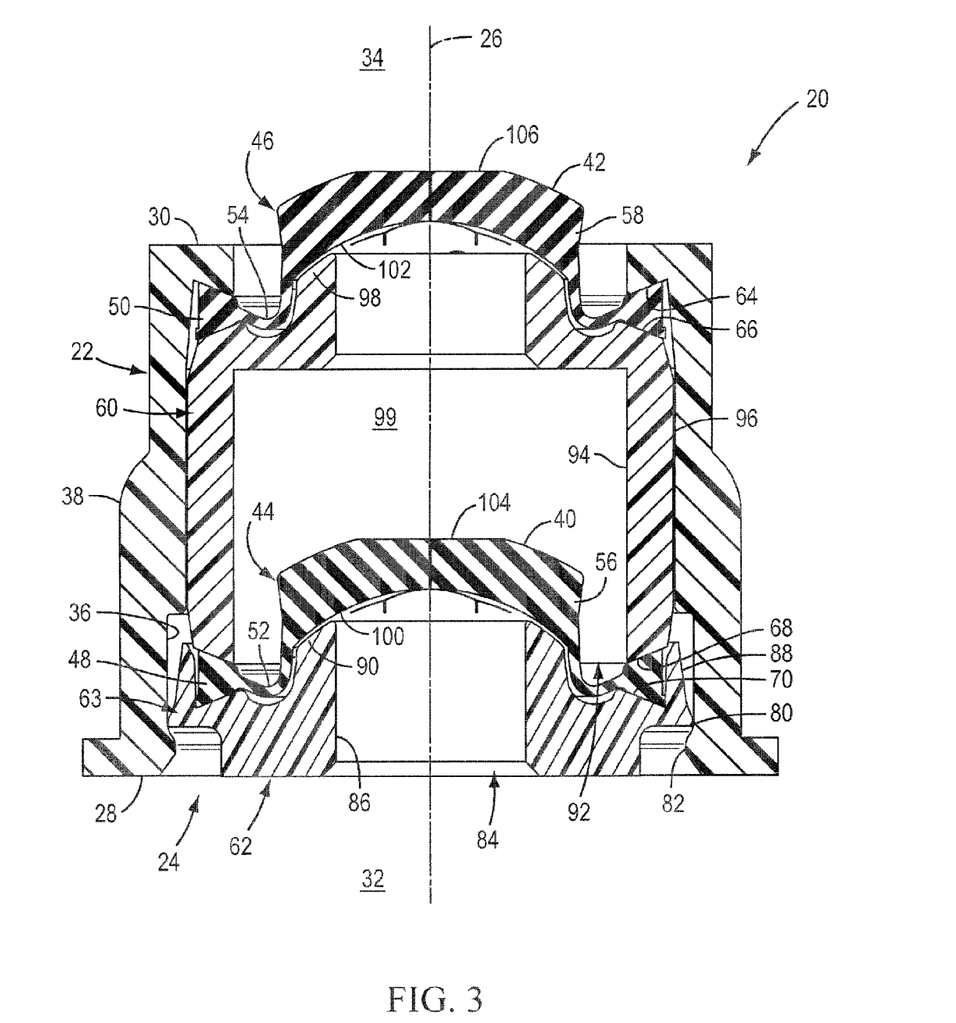
FIG. 3 is a section view taken along line 3-3 in FIG. 1.

As best seen in FIGS. 1-3, the system 20 includes a housing 22 defining a port 24 extending along a longitudinal axis 26 between an exterior end 28 of the housing 22 and an interior end 30 of the housing 22 to establish communication between an exterior environment, shown diagrammatically at 32, and an interior space, shown diagrammatically at 34. As best seen in FIG. 3, in the illustrated embodiment, the port 24 is defined by a stepped, cylindrical surface 36 that extends from one end 28 to the other end 30. The housing 22 further includes an exterior surface 38 that is configured for mounting in the structure for the intended application, with the illustrated embodiment showing the surface 38 as generally cylindrical for mounting in a medical port or cannula (not shown). The dual sealing system 20 further includes first and second flexible, resilient penetratable members 40 and 42, with the first penetratable member 40 extending across the port 24 at a first location along the axis 26, and the second penetratable member 42 extending across the port 24 at a second location along the axis 26. The penetratable members 40 and 42 are configured to seal the interior space 34 with respect to the exterior environment 32 in both a closed condition as shown in FIG. 3 wherein the probe 21 is not inserted into the dual sealing system 20 and an open or penetrated condition, wherein the probe 21 is either partially inserted into the sealing system 20, as shown in FIG. 6, or completely inserted in the sealing system 20, as shown in FIG. 7. In this regard, it is preferred that both of the penetratable members 40 and 42 be configured to seal around the probe 21 when it is inserted into the system 20, as shown in FIGS. 7 and 8, and that both of the penetratable members 40 and 42 be configured to create a seal after the probe 21 has been removed from the dual sealing system 20, as shown in FIG. 3. However, in some applications, it may be desirable to optimize the first penetratable member 40 for sealing around the probe 21 when the probe is inserted into the dual sealing system 20, and to optimize the second penetratable member 42 to create a seal after the member 42 has been penetrated by the probe 21 and the probe 21 has been removed. In this regard, the optimization of each of the penetratable members 40 and 42 will be highly dependent upon the details of each particular application, including the type of probe 21 used in the application, and may include optimization of the particular material used for each of the members 40 and 42, the durometer of the material of each of the members 40 and 42, the particular shape of each of the members 40 and 42, and/or the type, number and configuration of slits utilized in each of the members 40 and 42 to the extent that either of the members 40 and 42 include slits.

In the illustrated embodiment, the system 20 includes a pair of self-closing, slit-type valves 44 and 46 extending across the port 24, with each of the valves 44 and 46 having a corresponding peripheral attachment portion or flange 48 and 50, respectively. The valves 44 and 46 further include resilient sleeve portions 52 and 54 having a curved wall portion joined with a straight wall portion as viewed in longitudinal cross section along a plane container the longitudinal axis, respectively that extend laterally inwardly from the flanges 48 and 50 to respective head portions 56 and 58 of the valves 44 and 46. The head portions 56 and 58 define the respective penetratable member 40 and 42.

As best seen in FIGS. 3-5, the illustrated embodiment of the system 20 further includes a spacer 60 sandwiched in the housing 22 between the peripheral attachment portions 48 and 50, and a retainer 62 defining a retainer ring 63 that has a snap fit engagement with the housing 22 to retain the valves 44 and 46 and the spacer 60 within the housing 22 while clamping the flanges 48 and 50 in respective valves seats 64, 66, 68 and 70 provided in the housing 22, the spacer 60, and the retainer 62. In this regard, each of the flanges 48 and 50 have a generally dovetail-shaped, transverse cross section which defines a pair of frusto-conical surfaces that matingly engage corresponding frusto-conical surfaces provided in the corresponding valve seat 64, 66, 68 and 70. A lateral peripheral edge 80 of the retainer 62 is maintained in a snap fit engagement with an annular retaining bead 82 of the housing 22 that causes the retainer 62 to clamp the flanges 48 and 50 in their respective seats 64, 66, 68 and 70, thereby clamping the valves 44 and 46 and the spacer 60 within the housing 22. It should be understood that during assembly, the retainer ring 63 can be pushed past the retaining bead 82 because there is sufficient flexibility in the retainer ring 63 and retainer 62 and/or housing 22 to accommodate temporary, elastic deformation of the components as the edge 80 passes over, and inwardly beyond, the bead 82 to create a snap-fit engagement between the retainer ring 63 and housing 22 such that the valve flanges 48 and 50 are compressed at least slightly and clamped between the opposing frusto-conical surfaces of the corresponding seats 64, 66, 68, and 70 (FIG. 3). While a preferred form of mounting has been shown, the housing 22 and valves 44 and 46 could have other configurations, such as a different shape for the mounting flange 48 and 50 and seats 64, 66, 68, and 70, or such as a construction that eliminates the need for the spacer 60. Also, in some other arrangements, the valves 44 and 46 could be held in the housing 22 without a retainer ring 63. For example, the valves 44 and 46 could be held in the housing 22 by heat bonding, swaging of a portion of the housing 22 over the valve flange 60, adhesive, and/or a press fit, etc.

Again with reference to FIG. 3, the retainer 62 further includes a central passage 84 that is defined by a cylindrical surface 86, an annular wall 88 that surrounds the flange 48, and a nose 90 that is shaped to conform to the exterior side of the valve 44.

The spacer 60 further includes a central passage 92 defined by a stepped cylindrical surface 94, an exterior surface 96 that is shaped to closely conform to the surface 36 of the housing 22, and a nose 98 that is shaped to conform to the exterior side of the valve 46. As seen in FIG. 3, an enclosed volume 99 is defined in the central passage 92 of the spacer 60 between the valves 44 and 46. In some applications, it may be advantageous to provide a vacuum and/or a reduced pressure within the enclosed volume 99, or to fill the enclosed volume 99 with a fluent substance that can provide an advantage for the particular application in which the system 20 is intended, such as, for example, filling the enclosed volume 99 with a lubricant for the probe 21 to assist its passage through the system 20, or filling the enclosed volume 99 with an inert gas that can serve as an additional barrier between the exterior environment 32 and the interior space 34.

Preferably, the housing 22, the spacer 60, and the retainer 62 are each molded as a unitary structure from a suitable material, including a suitable plastic or elastomer. However, in some applications it may be desired to form one or more of these components by other methods, such as, for example, machining or extruding.

Each valve 44 and 46 is preferably molded as a unitary structure from material which is flexible, pliable, elastic, and resilient. This can include elastomers, such as a synthetic, thermosetting polymer, including silicone rubber, such as the silicone rubber sold by Dow Corning Corp. in the United States of America under the trade designation SILASTIC 99-595-HC. Another suitable silicone rubber material is sold in the United States of America under the designation Wacker 3003-40 by Wacker Silicone Company. Both of these materials have a hardness rating of 40 Shore A. Other suitable silicone rubber materials are sold by Dow Corning under designations LC-70 and 9280-70. Both of these materials preferably have a hardness ratio of 70 Shore A. The valves 44 and 46 can also be molded from other thermosetting materials or from other elastomeric materials, or from thermoplastic polymers or thermoplastic elastomers, including those based upon materials such as thermoplastic propylene, ethylene, urethane, and styrene, including their halogenated counterparts.

Figure 9:
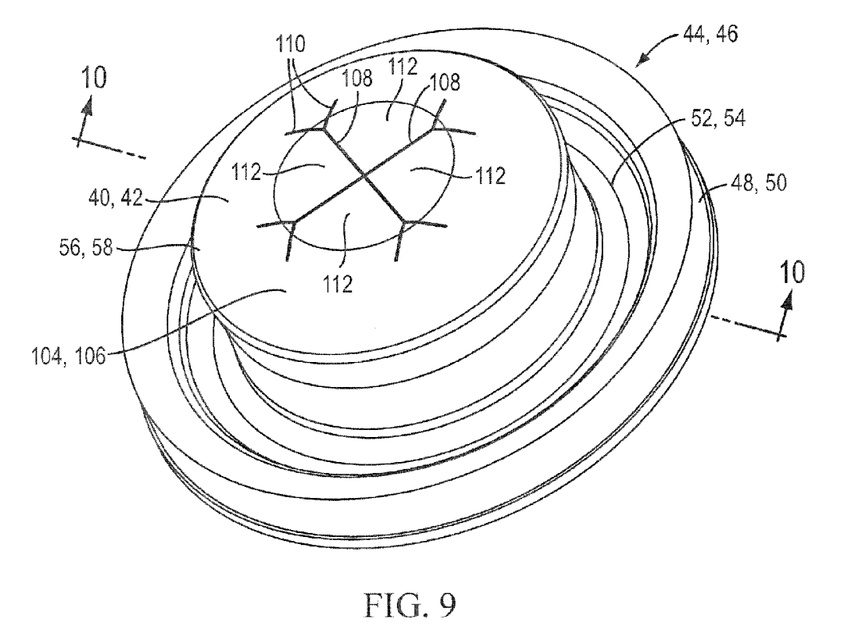
FIG. 9 is an enlarged isometric view from the interior side of a valve component utilized in the dual sealing system of FIG. 1.

Each valve 44 and 46 has a normally closed, rest position or configuration shown in FIGS. 1-5, 9 and 10. With the insertion of the probe 21, each of the valves 44 and 46 can be forced to one or more open positions or configurations, as shown in FIGS. 6-8. As best seen in FIGS. 3 and 9, the penetratable members 40 and 42 as defined by the heads 56 and 58 have respective exterior sides 100 and 102 and respective interior sides 104 and 106. In the illustrated embodiments, when the valves 44 and 46 are in the closed state, the exterior sides 100 and 102, respectively, are concave and arcuate in shape, preferably semispherical, and the interior sides 104 and 106, respectively, are convex and arcuate in shape with a flattened central portion. In this regard, while preferred forms of the penetratable members 40 and 42 and heads 56 and 58 are shown herein, it should be understood that other configurations may be desirable depending upon the specific parameters and requirements of each particular application. For example, in some applications it may be desirable for one or more of the surfaces 100, 102, 104, and 106 to be a completely flat surface.

Figure 10:
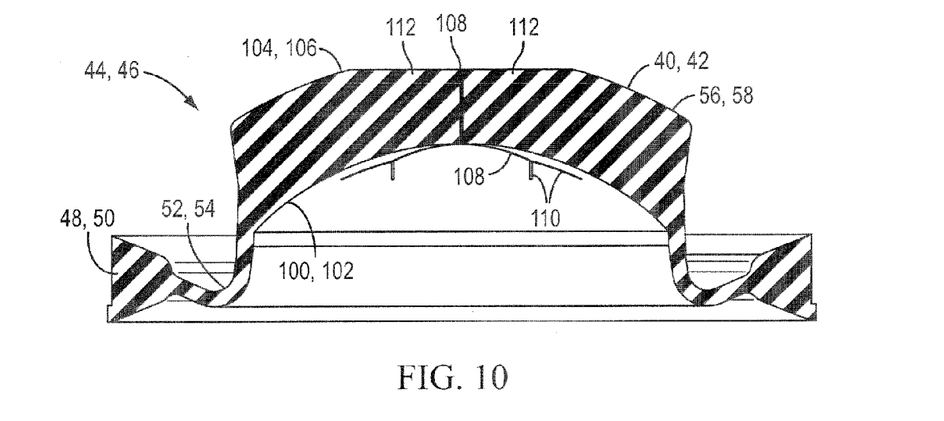
FIG. 10 is a section view taken along line 10-10 in FIG. 9.

As best seen FIGS. 9 and 10, each of the penetratable members 40 and 42 has planar, intersecting, self-sealing slits 108 which together define a closed orifice when the member 40, 42 is in a closed condition. For the embodiment shown in FIGS. 9 and 10, the slits 108 are normal to each other and equal in length and further include pairs of planar, intersecting, self-sealing slits 110 that form a V at each end of the slits 108, thereby forming a "snowflake" pattern of slits best seen in FIG. 9. The slits 108 and 110 define four, generally sector-shaped, equally sized flaps or petals 112 in the member 40,42. The flaps or petals 112 may be also characterized as "openable regions" or "openable portions" of the member 40,42. Each flap or petal 112 has a pair of diverging transverse faces defined by the slits 108,110 and each transverse face seals against a confronting transverse face of an adjacent petal 112 when the member 40, 42 is closed.

The member 40,42 can be molded with the slits 108 and 110. Alternatively, the slits 108 and 110 can be subsequently cut into the member 40,42 by suitable conventional techniques. As another alternative, the member 40,42 can be weakened along frangible lines corresponding to the slits 108 and 110 such that the slits 108 and 110 are formed by the first, initial penetration of the member 40,42 with the probe 21. However the slits 108 and 110 are formed, the orifice should be closed when the member 40, 42 is in an unconstrained or as-molded condition. In operation, the petals 112 can be forced open inwardly toward the interior space 34 from the intersection point of the slits 108,110 when a sufficient force is applied to the exterior side 100,102 of the member 40,42 by the probe 21.

FIGS. 6 and 7 illustrate an example of the members 40 and 42 opening inwardly with the probe 21 being partially inserted toward the interior 34 in FIG. 6 and being completely inserted in FIG. 7 to access the interior space 34. The open petals 112 accommodate the penetration of the end of the probe 21 into the interior space 34. The petals 112 seal around the periphery of the probe 21 in a substantially liquid-tight and/or air-tight manner. When the probe 21 is withdrawn from the members 40 and 42 by movement away from the interior 34 and toward the exterior 32, the inherent resiliency of the members 40 and 42 and the petals 112 return the orifice to the closed condition. In this regard, as best seen in FIG. 8, as the probe 21 is withdrawn, the nose 90 of the retainer 62 supports the member 40 by abutting the surface 100 to prevent the petals 112 from inverting, and the nose 98 of the spacer 60 supports the member 42 by abutting the surface 102 to prevent the petals 112 from inverting. Further in this regard, it should be understood that this support function will be enhanced if the passages 84 and 92 in the noses 90 and 98 of the retainer 62 and spacer 60 closely conform to the exterior shape of the probe 21. While this support function is preferred, it may be not be required in all applications, or may not be required for both members 40 and 42 in all applications. For example, in some applications, it may be desirable to eliminate the support function for the member 40 while retaining the support function for the member 42 to help insure that the member 42 seals against any positive pressure differential after the probe 21 is withdrawn from the member 42.

It is to be understood that the orifice of the members 40 and 42 may be defined by structures other than the illustrated straight slits 108,110. The slits may have various different shapes, sizes and/or configurations in accordance with the requirements and parameters of each particular application. For example, the orifice may include just one slit, or may also include four or more intersecting slits. It should also be understood that while the penetratable members 40 and 42 have been shown in the illustrated embodiments as being defined by the head portions 56 and 58 of the valves 44 and 46, in some applications it may be desirable for either or both of the penetratable members 40 and 42 to be defined on their own, without the provision of a valve 44,46 having an associated head portion 56,58. Furthermore, while the illustrated embodiment shows a pair of valves 44 and 46 that are spaced by the spacer 60, in some applications it may be desirable for the penetratable members 40 and 42 to be provided as part of a single, unitary construction that is inserted into the housing 22, or even as a single unitary structure with the housing 22.

It should be appreciated that the member 42 prevents the member 40 from being subjected to full pressure differential between the interior space 34 and the exterior environment 32 when the probe 21 is inserted through both members 40 and 42, and when the probe 21 is withdrawn from the member 42 but still penetrating the member 40. It should further be appreciated that by providing the dual penetratable members 40 and 42 spaced along the axis 26, the exterior-most member 40 can be, if desired, optimized to provide a seal around the probe 21 and the interior-most member 42 can be optimized to provide a seal when the probe 21 is withdrawn. This is particularly advantageous if the interior space 34 has a positive pressure differential with respect to the exterior environment 32.

It will be readily observed from the foregoing detailed description of the invention and from the illustrations thereof that numerous other variations and modifications may be effected without departing from the true spirit and scope of the novel concepts or principles of this invention.

The invention claimed is:

1. A dual sealing system for use with a probe, said system comprising:
   a housing defining a port extending along a longitudinal axis between an exterior end of the housing and an interior end of the housing to establish communication between an exterior environment and an interior space;
   a first flexible, resilient penetratable member extending across the port at a first location along the axis, the first penetratable member configured to create a seal around the probe with the probe inserted therethrough;
   a first connector sleeve extending between the first penetratable member and the housing, the first connector sleeve defined by a first flexible, resilient tubular wall, the first tubular wall, as viewed in longitudinal cross section along a plane containing the longitudinal axis, having a curved wall portion joined with a straight wall portion;
   a second flexible, penetratable member extending across the port at a second location along the axis spaced toward the interior end from the first location, the second penetratable member configured to create a seal after having been penetrated by the probe and the probe has been removed from the second penetratable member; and
   a second connector sleeve extending between the second penetratable member and the housing, the second connector sleeve defined by a second flexible, resilient tubular wall, the second tubular wall, as viewed in longitudinal cross section along a plane containing the longitudinal axis, having a curved wall portion joined with a straight wall portion.

2. The dual sealing system of claim 1 wherein at least one of he penetratable members comprises:
   at least one self-sealing slit through the penetratable member; and
   confronting, openable portions along the slit to define a normally closed orifice in an unconstrained condition wherein the openable portions can move toward the interior space to an open orifice configuration.

3. The dual sealing system of claim 2 wherein the at least one self-sealing slit comprises two self-sealing slits extending transverse to each other.

4. The dual sealing system of claim 1 wherein:
the first penetratable member is configured to create a seal after having been penetrated by the probe and the probe has been removed from the first penetratable member; and
the second penetratable member is configured to create a seal around the probe with the probe inserted therethrough.

5. The dual sealing system of claim 1 wherein the first and second penetratable members are identical in construction.

6. The dual sealing system of claim 1 further wherein the first and second penetratable members are separate components and wherein the system further comprises a spacer extending between the first and second penetratable members within the housing.

7. The dual sealing system of claim 6 further comprising a retainer (62) engaged with the housing to retain the penetratable members and the spacer within the housing.

8. The dual sealing system of claim 1 wherein the port and the penetratable members have circular cross sections transverse to the axis.

9. The port closure system of claim 1 wherein each of the penetratable members has an interior side facing toward the interior space and defined by a convex surface.

10. The system of claim 1 wherein each of the penetratable members has an exterior side facing toward the exterior environment and defined by a concave surface.

11. The system of claim 10 wherein the concave surface is semispherical.

12. The system of claim 1 further comprising first and second valves, each of the valves having a peripheral attachment portion mounted to the housing;
the first valve further comprising the first penetratable member in the form of a first flexible, resilient head, and the first connector sleeve extending between the first head and the peripheral attachment portion of the first valve, and
the second valve further comprising the second penetratable member in the form of a second flexible, resilient head, and the second connector sleeve extending between the second head and the peripheral attachment portion of the second valve.

13. The system of claim 12 wherein each of the heads has at least one self-sealing slit through said head and confronting, openable portions along said slit to define an initially closed orifice wherein said valve head openable portions can move generally in a first direction toward said interior space to an open configuration, each of the valves having an initial, manufactured configuration in which said valve orifice is closed.

14. The system of claim 13 wherein the at least one self-sealing slit of each head comprises two self-sealing slits extending transverse to each other.

15. The system of claim 13 wherein the housing further comprises a seat around the port and wherein the peripheral attachment portion of the second valve is engaged in said seat.

16. The system of claim 15 further comprising a spacer engaged with the peripheral attachment portions of the first and second valves and sandwiched in the housing between the peripheral attachment portions of the first and second valves.

17. A dual sealing system for use with a probe, said system comprising:
a housing defining a port extending along a longitudinal axis between an exterior end of the housing and an interior end of the housing to establish communication between an exterior environment and an interior space;
a first flexible resilient penetratable member extending across the port at a first location along the axis, the first penetratable member configured to create a seal around the probe with the probe inserted therethrough;
a first connector sleeve extending between the first penetratable member and the housing, the first connector sleeve defined by a first flexible, resilient tubular wall;
a second flexible, penetratable member extending across the port at a second location along the axis spaced toward the interior end from the first location, the second penetratable member configured to create a seal after having been penetrated by the probe and the probe has been removed from the second penetratable member;
a second connector sleeve extending between the second penetratable member and the housing;
further comprising first and second valves each of the valves having a peripheral attachment portion mounted to the housing;
the first valve further comprising the first penetratable member in the form of a first flexible, resilient head, and the first connector sleeve extending between the first head and the peripheral attachment portion of the first valve, and
the second valve further comprising the second penetratable member in the form of a second flexible, resilient head and the second connector sleeve extending between the second head and the peripheral attachment portion of the second valve;
each of the heads has at least one self-sealing slit through said head and confronting, openable portions along said slit to define an initially closed orifice wherein said valve head openable portions can move generally in a first direction toward said interior space to an open configuration, each of the valves having an initial, manufactured configuration in which said valve orifice is closed;
further comprising a spacer sandwiched in the housing between the peripheral attachment portions of the first and second valves,
wherein the housing further comprises a seat around the port and wherein the peripheral attachment portion of the second valve is engaged in said seat; and
wherein the spacer further comprises a seat and wherein the peripheral attachment portion of the first valve is engaged in the seat.

18. The system of claim 17 further comprising a retainer ring in snap-fit engagement with said housing to clamp the peripheral attachment portions in their respective seats.

19. The system of claim 12 wherein the first and second valves have identical constructions.

20. The system of claim 12 wherein each of the valves is initially separate from, but subsequently attachable to, the housing.

* * * * *